United States Patent [19]
Wood et al.

[11] Patent Number: 5,190,536
[45] Date of Patent: Mar. 2, 1993

[54] SUBMERSIBLE LENS FIBEROPTIC ASSEMBLY FOR USE IN PDT TREATMENT

[75] Inventors: Leroy Wood, Buffalo; Donn Boyle, No. Tonawanda; William R. Potter, Grand Island, all of N.Y.

[73] Assignee: Health Research, Inc., Buffalo, N.Y.

[21] Appl. No.: 839,724

[22] Filed: Feb. 19, 1992

Related U.S. Application Data

[63] Continuation of Ser. No. 461,636, Jan. 8, 1990, abandoned, which is a continuation-in-part of Ser. No. 268,723, Nov. 8, 1988, Pat. No. 5,111,821.

[51] Int. Cl.$^5$ ............................................. A61N 5/06
[52] U.S. Cl. ...................................... 606/16; 606/17; 128/398; 385/35
[58] Field of Search ................. 128/665, 397-398, 128/634; 606/15-17; 385/35

[56] References Cited

U.S. PATENT DOCUMENTS

| | | | |
|---|---|---|---|
| 3,843,228 | 10/1974 | Yoshiyagawa et al. | 350/96.31 |
| 4,470,407 | 9/1984 | Hussein | 128/6 |
| 4,515,444 | 5/1985 | Prescott et al. | 350/96.31 |
| 4,608,980 | 9/1986 | Aihara | 606/16 |
| 4,649,151 | 3/1987 | Dougherty et al. | |
| 4,660,925 | 4/1987 | McCaughan, Jr. | |
| 4,676,231 | 6/1987 | Hisazumi et al. | 606/15 |
| 4,693,556 | 9/1987 | McCaughan, Jr. | |
| 4,860,743 | 8/1989 | Abela | 606/15 |
| 4,865,029 | 9/1989 | Pankratov et al. | 606/4 |

Primary Examiner—Ruth S. Smith
Attorney, Agent, or Firm—James F. Mudd; Michael L. Dunn

[57] ABSTRACT

A submersible lens fiberoptic assembly for PDT treatment includes an optical fiber, a fiber jacket, a ball lens made of zirconia and a housing. This fiberoptic assembly is simple and inexpensive to manufacture, and has a high quality of output light beam. A submersible lens fiberoptic assembly for PDT treatments is also disclosed which uses a hemisphere ball lens for treatment of areas inaccessible to a normal "forward looking" lens.

5 Claims, 5 Drawing Sheets

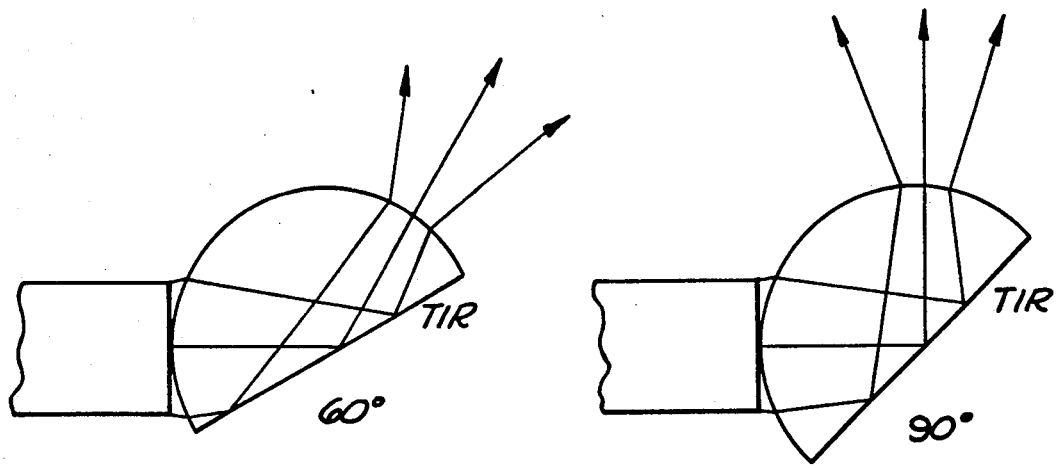
fig.9a.
fig.9b.
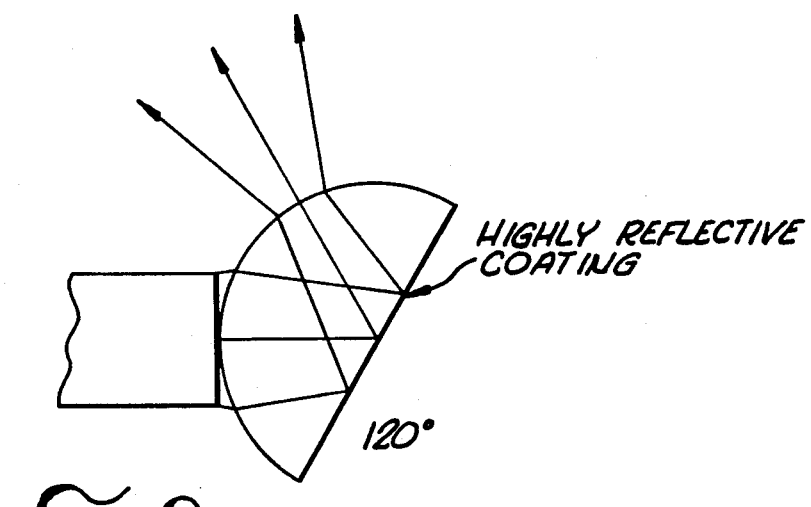
fig.9c.
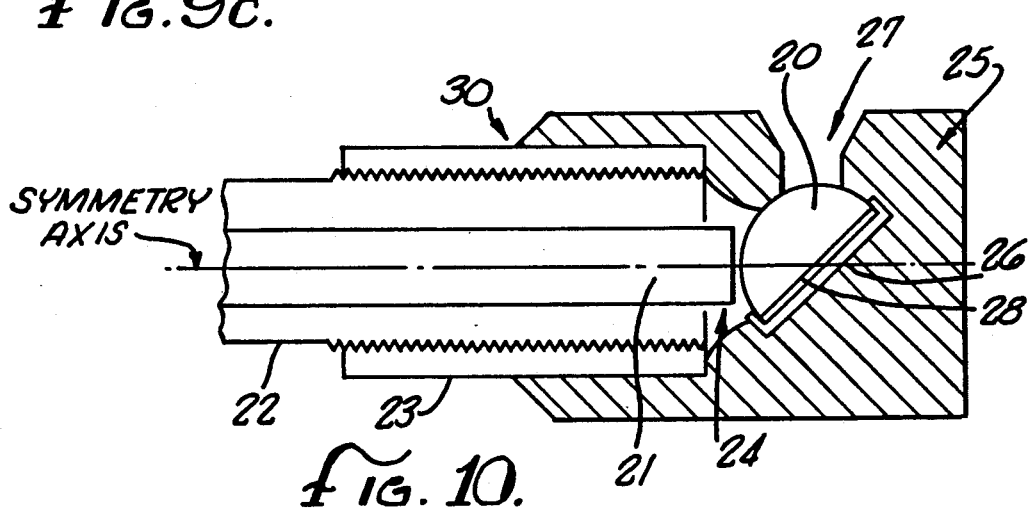
fig.10.

SUBMERSIBLE LENS FIBEROPTIC ASSEMBLY FOR USE IN PDT TREATMENT

The work relating to the invention described herein was performed under National Institutes of Health grant No. 5R01 CA16717.

CROSS REFERENCES TO RELATED APPLICATIONS

This is a continuation of application Ser. No. 461,636, filed Jan. 8, 1990, now abandoned, which is a continuation-in-part of application Ser. No. 268,723, filed Nov. 8, 1988, now U.S. Pat. No. 5,111,821.

BACKGROUND OF THE INVENTION

The present invention relates to a submersible lens fiberoptic assembly for use in a biological environment, and especially to a submersible ball lens fiberoptic assembly for photodynamic therapy treatments (hereinafter referred to as PDT) for transferring radiation from an optical fiber to surrounding tissue.

There are three existing types of fiberoptics used for light delivery in PDT treatments. These three known arrangements are shown in FIGS. 1A, 1B and 1C.

FIG. 1A shows an arrangement known as a cylindrical diffuser. In this, a cylindrical optical element 11 is butted against an optical fiber 12, and functions to cylindrically diffuse light coupled into it via the optical fiber.

FIG. 1B shows a prior art arrangement known as a spherical diffuser. In this, a spherical optical element 13 is coupled to an optical fiber 14 by an optical coupling 15, and functions to spherically diffuse light from the optical fiber into surrounding tissue.

One disadvantage of the prior art constructions shown in FIGS. 1A and 1B is that every spot light source on the diffusing material emits light in a random direction; that is, there is no localization control over the specific tissue being treated.

A third prior art arrangement is shown in FIG. 1C, this being an arrangement known as a submersible microlens. In the arrangement of FIG. 1C light rays are emitted at a controlled divergence due to the functions of lenses. In this construction, a housing 16 encloses a miniature lens 17, and the housing is closed by a transparent cover plate 18. The end of an optical fiber 19 is positioned at the back focal point of the lens 17. The location of the back focal point of the lens is influenced by the index of refraction of the lens and of the medium in contact with the lens and the optical fiber surface. In the construction shown in FIG. 1C, the back focal point is fixed by sealing the fiber and lens in air through use of the housing 16 and window or cover plate 18. When this assembly is submerged in water or a saline solution, the beam divergence is reduced but the end or face of the optical fiber remains in focus since the medium surrounding the curved refracting surface of the lens is unchanged.

The ideal assembly for coupling radiation from an optical fiber into tissue is one which produces a highly divergent beam of light whose cross section everywhere, in air or water, is a magnified image of the optical fiber end or face. While the arrangement of FIG. 1C does achieve many of these objectives, the construction is complicated and accordingly expensive to manufacture.

OBJECTS AND SUMMARY OF THE INVENTION

It is an objective of the present invention to provide a simplified, inexpensive and easily manufactured submersible lens fiberoptic assembly.

It is another objective of the present invention to provide a novel submersible lens fiberoptic assembly which can produce a highly divergent beam of light whose cross section everywhere, in water or in air, is very close to a magnified image of the fiber end.

It is another objective of the present invention to provide a submersible lens fiberoptic assembly which does not require the use of any optical window for isolating lens components from the medium in which the assembly is used.

It is a still further objective of the present invention to provide a submersible lens fiberoptic assembly which can be used in conjunction with side-looking fiberoptic scopes for treatment of areas inaccessible to a "forward looking" lens.

Briefly, in accordance with one embodiment of the invention, a submersible lens fiberoptic assembly for use in a biological environment, especially in PDT treatments, has an optical fiber with an end for emitting light energy, a fiber jacket for fixing and protecting the optical fiber, a lens made of zirconia for transferring the light beam and controlling the beam divergence, and a housing for fixing the fiber jacket and the lens. As zirconia has good properties of resisting mechanical and thermal shock, there is no need to use a window as in the case of the prior art. In a preferred embodiment, the lens is a ball lens, and the fiber jacket and housing is in a threaded connection so that the distance between the optical fiber face and the ball lens can be adjusted by simply rotating the housing on the jacket. Since the lens is a ball shape, the assembly has good divergent and image formation properties. In another embodiment, the present invention provides a novel submersible lens fiberoptic assembly for use in PDT treatments using a hemisphere lens with its spherical surface facing the optical fiber end for transferring the light beam to areas which are inaccessible to a normal "forward looking" lens.

BRIEF DESCRIPTION OF THE DRAWINGS

FIGS. 9A, 9B and 9C show schematically three different arrangements of another preferred embodiment of the present invention which can deliver the light beam to the treatment areas inaccessible to a "forward looking" lens.

FIG. 10 shows schematically an embodiment of the housing having a top cover portion used in a side looking submersible lens fiberoptic assembly of the present invention.

DETAILED DESCRIPTION

Figure 1A:
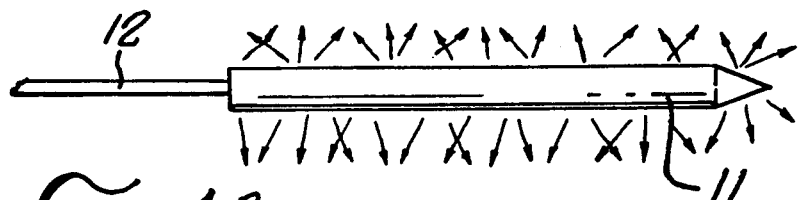
FIGS. 1A, 1B and 1C show three different types of prior art assemblies used for light delivery in PDT treatments.
Figure 1B:
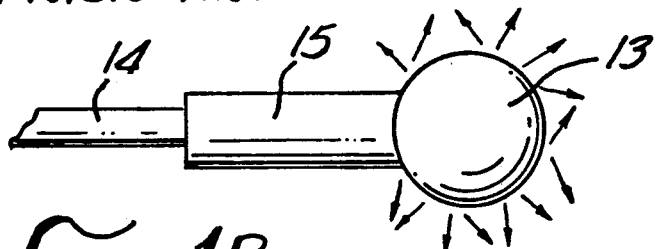
Figure 1C:
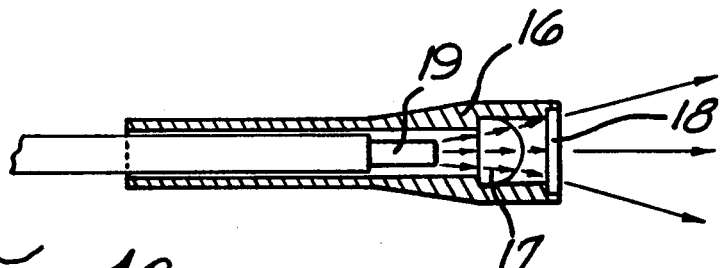
Figure 2:
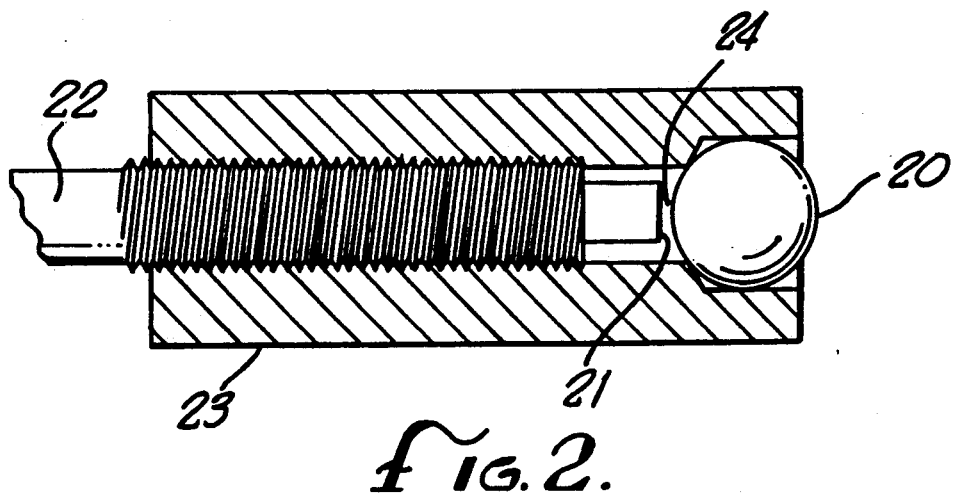
FIG. 2 shows a preferred embodiment of the submersible ball lens fiberoptic assembly of the present invention.

As mentioned above, one of the important objectives of the present invention is to provide a simplified, inexpensive submersible lens fiberoptic assembly which requires a minimum in manufacturing equipment and produces a highly divergent beam of light having a symmetrical cross section along its length, both in air and water. Referring now to FIG. 2, a preferred embodiment of the submersible lens fiberoptic assembly of the present invention includes a ball lens 20, an optical fiber 21 having a fiber jacket 22 and a cylindrical housing 23.

The ball lens 20 is preferably made of zirconia because of its mechanical, thermal and optical properties. Specifically, zirconia is a very hard material. If a zirconia ball is placed on a lab table and struck with a carpenter's hammer, for example, the table top acquires a dent, but there is no visible damage to the ball. This ability to withstand rough handling simplifies the assembly procedure. The cylindrical housing 23 can be made of metal, such as brass. One end of the metal housing is drilled to take the press-fitted ball lens 20. The metal housing 23 and the fiber jacket 22 are preferably threadedly coupled so that the distance between the optical fiber face and the ball lens can be adjusted precisely by simply rotating the housing 23. The pressfit and the tight thread on the fiber jacket make a water tight seal to the air chamber (generally indicated by reference numeral 24) on the input side of the ball. Care must be taken to insure that this volume is free of particles during assembly since the ball lens produces an enlarged image of particles lying on the face of the fiber.

The exposed surface of the ball lens 20 needs no special protection or cleaning procedure. This was demonstrated in an experiment wherein a ball lens fiberoptic was coupled to an argon pumped dye laser and submerged in a test tube of human blood. The dye laser power was increased until the blood adjacent to the lens surface was boiling vigorously. The ball lens fiberoptic was withdrawn and allowed to "smoke." The baked blood was scraped from the lens surface with a knife edge and the surface was wiped clean with an alcohol soaked gauze. The focused spot using this ball lens appeared to be the same as before the test.

In accordance with one specific embodiment, the ball lens 20 is a 1 mm diameter precision optical sphere made of zirconia, and the metal housing or cylinder 23 is drilled through from the opposite end to take a 120 thread per inch tap. Suitable zirconia spheres are commercially available from Precomp Inc., of Great Neck, N.Y. The metal housing is threaded into the jacket 22 of a 400 micrometer diameter optical fiber until the polished fiber end is in contact with the sphere, and then backed off one-half turn. The back focal point for the submerged ball lens assembly is 108 micrometers from the surface of the ball lens. This is a half turn of the thread. The back focal point for the lens in air is inaccessible, being 33 micrometers inside the ball. However, the fiber end is nearly focused in air and appears sharp in water, even if the fiber is in contact with the ball.

Figure 3:
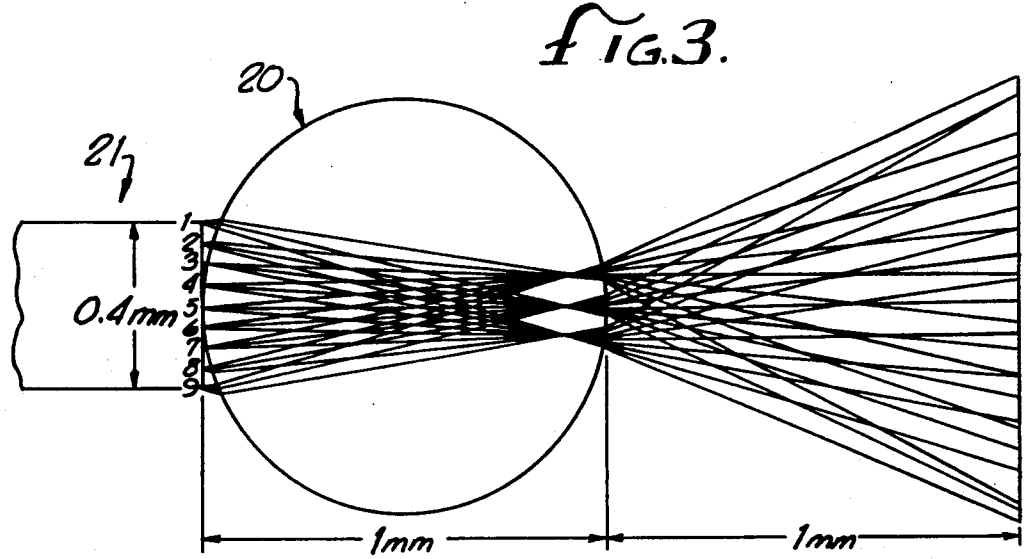
FIG. 3 is a schematic ray diagram of a 1 mm zirconia ball lens in air of the submersible ball lens fiberoptic assembly of the present invention.
Figure 4:
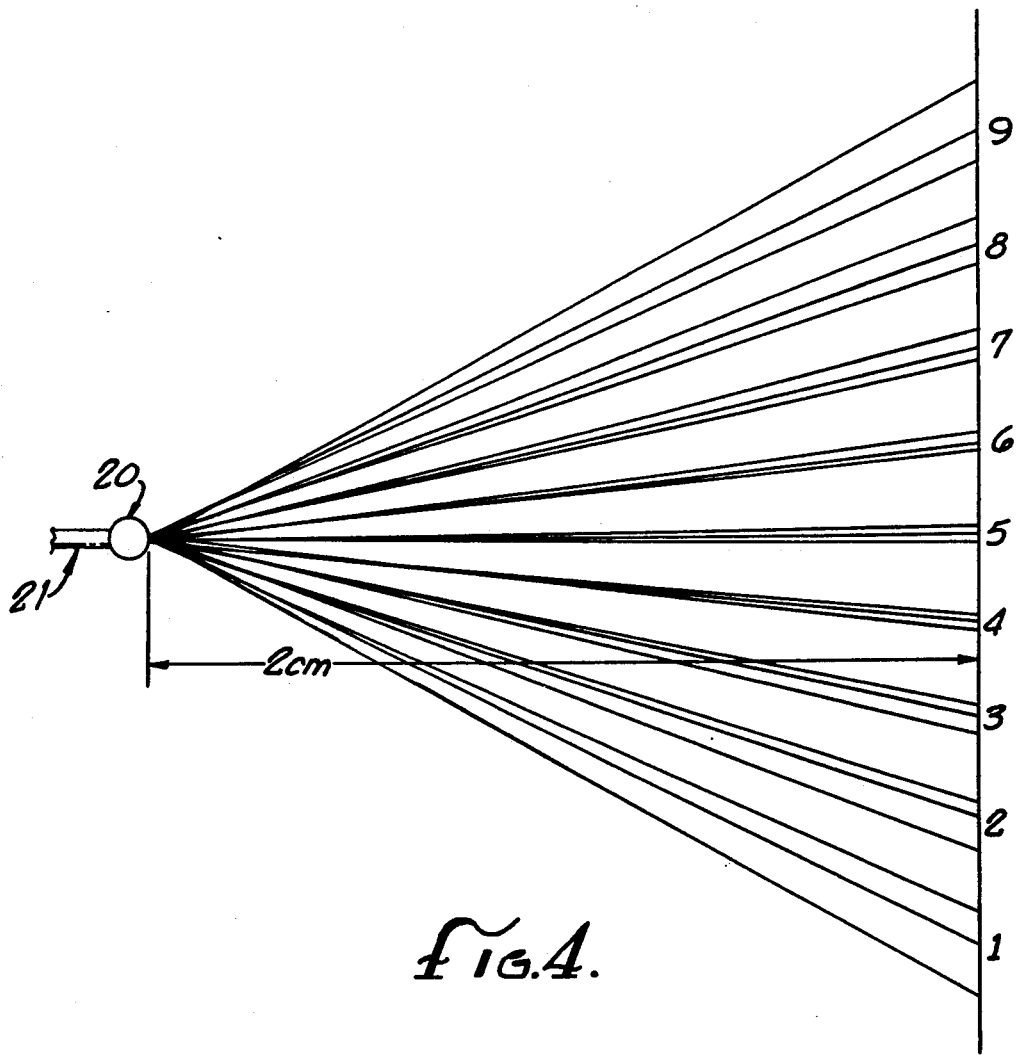
FIG. 4 shows schematically the ray trace of the output beam of a 1 mm zirconia ball lens in air.

The passage of light through the ball lens in air is demonstrated by the tracing of oblique meridonal rays as shown in FIGS. 3 and 4. The wavelength is 630 nm, for which the index of refraction of zirconia is 2.152. FIG. 3 is drawn on a scale of 100× and shows the light field in and near the ball. FIG. 4 is drawn on a scale of 10× and shows the beam for a distance of 2 cm from the lens.

The fiber is in contact with the ball in FIG. 3. Each point on the fiber surface is assumed to emit light into a cone with an apex angle given by the numerical aperture (N.A.) of the fiber. (N.A. is equal to the sine of half the apex angle.) Nine such points are labeled in the figure. Three rays from each point are drawn to show how the ball lens forms a focused image of the fiber end.

The ray traces are symmetrical about the optical axis (the line through the center of the sphere and perpendicular to the fiber face). All rays from the fiber having a common direction are focused by the input surface at a point inside the ball. Three such focal points are shown in FIG. 3 for the three rays of the cone. This focusing of the rays inside the lens occurs because the lens is spherical, its index of refraction is greater than 2, and the input surface of the sphere is in air. The light beam has its smallest diameter inside the sphere. The rays diverge from the focal points and are refracted at the output surface to form a more (in air) or less (in water) rapidly diverging beam.

The rays of the output beam near the lens in FIG. 3 are extended in FIG. 4 into the far field. The points of origin of the rays are indicated by the numbers on the right of the drawing. The rays from any point on the fiber face appear in the output beam as nearly parallel rays and are on the opposite side of the optical axis. For example, the three diverging rays from the top of the fiber in FIG. 3 appear in FIG. 4 as three nearly parallel rays at the bottom of the beam. Thus, any cross section of the beam in the far field of the lens is a magnified, inverted, nearly focused image of the fiber face. Therefore, there is no need for a window on the lens as is the case with the prior art.

Approximate but useful expressions can be derived from paraxial ray equations for the output beam divergence and the beam diameter at the output surface of the ball lens. These equations show how physical properties of the fiber, ball lens and medium in which the ball lens is submerged determine output beam parameters. The equations are:

$$U = \frac{360}{\pi} \frac{D_f}{D_b} \left(1 - \frac{2}{n} + \frac{1}{n^2}\right) \quad (1)$$

$$D_o = \left(1 - \frac{2}{n}\right)D_f + \frac{2}{n} D_b (N.A.) \quad (2)$$

Where
  $U$ = full angle beam divergence in degrees
  $D_f$ = optical fiber diameter $D_b$ = ball lens diameter n = index of refraction of the ball lens material, must be greater than or equal to 2

$n^1$ = index of refraction of medium in which lens is submerged, is equal to 1 for air, 1.33 for water $D_o$ = beam diameter at output surface of the ball N.A. = the numerical aperture of the fiber in air A practical application of equation (2) is the calculation of the beam intensity (watts/cm²) at the exposed surface of the ball lens. For a 1 mm diameter ball lens of zirconia and a 400 micron diameter fiber with a numerical aperture of 0.22, the beam diameter at the ball surface is 0.23 mm. Eighty milliwatts are required to treat a 1 cm diameter tumor at a power density of 100 mW/cm². The beam intensity at the ball surface calculates to be 190 watts/cm², a substantial energy flux. According to equation (1), the beam intensity drops to 100 mW/cm² at 11 mm from the lens in air.

Figure 5:
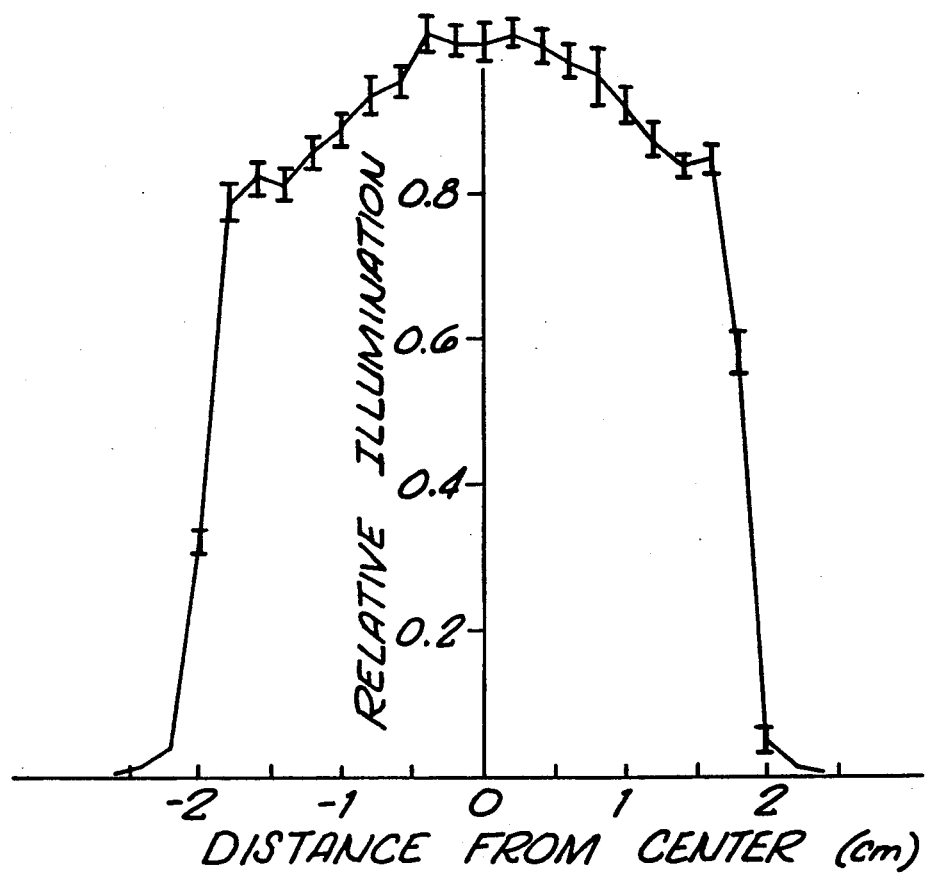
FIG. 5 is a diagram of the light distribution across a spot at 4.1 cm from a 1 mm diameter zirconia ball lens of the submersible ball lens fiberoptic assembly of the present invention.

The focused fiber end or spot appears very uniform to the eye. FIG. 5 is a plot of the measured light distribution across a spot at 4.1 cm from a 1 mm ball lens. The ball lens fiber was coupled to a helium-neon laser (633 nm wavelength) whose output was chopped at 1.5 kHz. The instrumentation consisted of a model 4010 Laserguide fiberoptic light guide, a photodetector, an amplifier phase locked to the 1.5 kHz signal, and a digital voltmeter. The light guide is a spherical diffuser normally used in PDT treatments of the bladder. It produces a spherically symmetric light field from a 1.7 mm diameter sphere of light diffusing material. Used in reverse it collects light from almost all directions.

Measurements were made every 2 mm across the beam. Each scan was repeated five times. The measured values were averaged and normalized with respect to the center value. The data are plotted in FIG. 5 with ± one sigma error bars. The illumination is 80% or better of the maximum value over most of the beam cross section. The distribution is not exactly symmetrical because the ball and fiber were not perfectly aligned. The peaks near the center and the edge may be due to multiple reflections.

It should be pointed out that the material costs are low for the construction of this invention, as shown in FIG. 2. Five hundred of the 1 mm diameter balls were purchased from Precomp Inc. for less than 40¢ each. The manufacturer's tolerances are ±1 micrometer on the diameter and one-quarter wave or better at 587 nm on the sphericity. The 400 micron diameter optical fiber was purchased from Ensign-Bickford Optics at $4 per meter. This fiber has a hard polymer cladding and a tefzel jacket. It is a very durable fiber.

Figure 6:
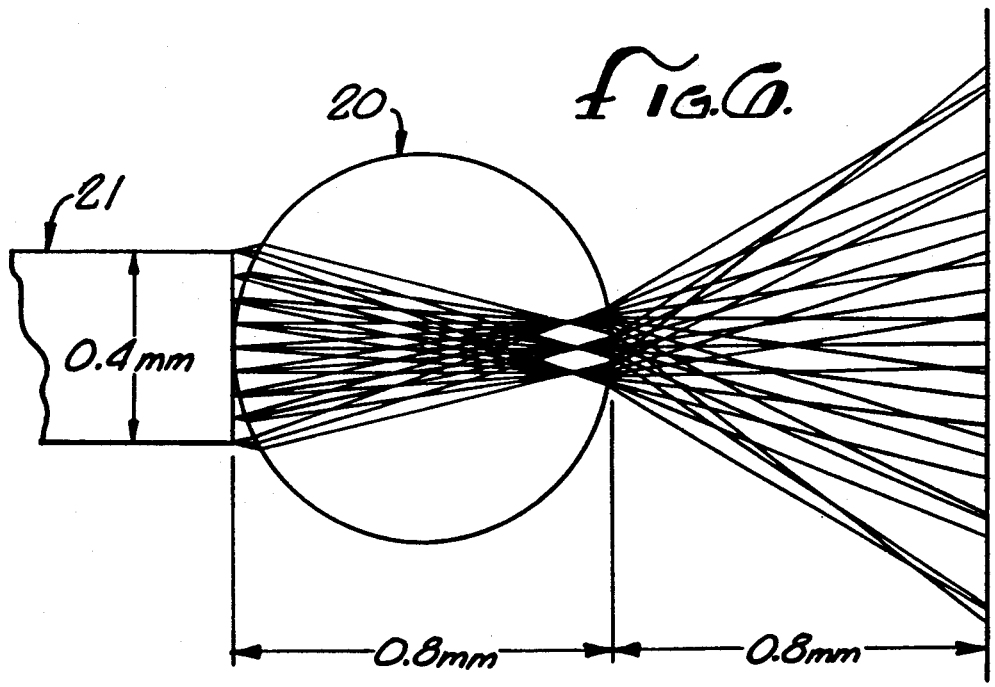
FIG. 6 is a schematic ray diagram of an 0.8 mm diameter zirconia ball lens in air of present invention.
Figure 7:
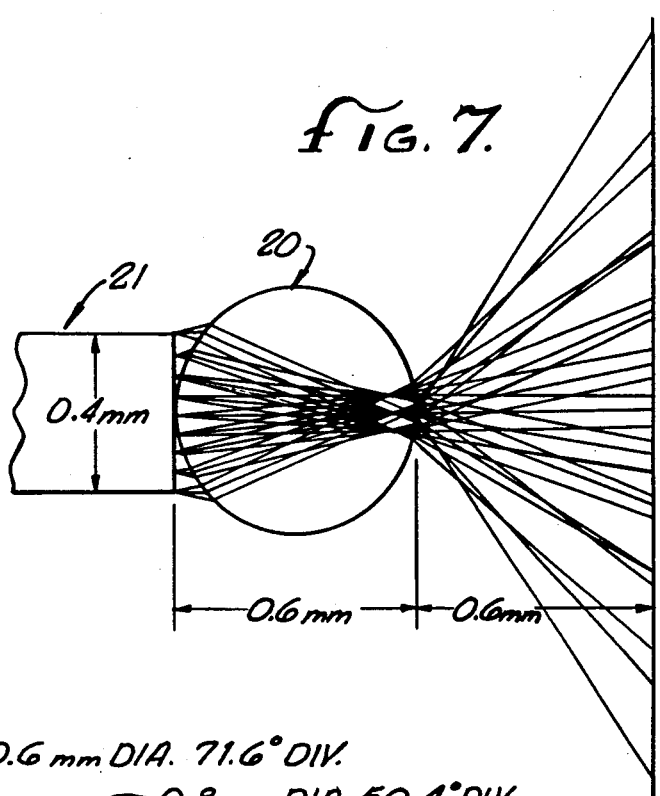
FIG. 7 is a schematic ray diagram of an 0.6 mm diameter zirconia ball lens in air of the present invention.

Smaller diameter balls produce beams of greater divergence as shown in FIGS. 6 and 7, relating respectively to 0.8 mm and 0.6 mm ball lens. The interior focal points are not as well defined in the 0.6 mm ball lens as in the 1 mm ball lens. This may indicate a fall-off in image quality with increasing curvature of the refractory surface.

The trace of the horizontal ray emitted from the edge of the fiber is used to define the output beam size. The angle which this ray makes with the optical axis after refraction at the output surface is the half-angle beam divergence. This ray appears to come from a point on the optical axis close to the output surface of the sphere. Therefore, the beam diameter at any distance from the lens is given by twice the product of this distance and the tangent of the half angle divergence.

Figure 8A:
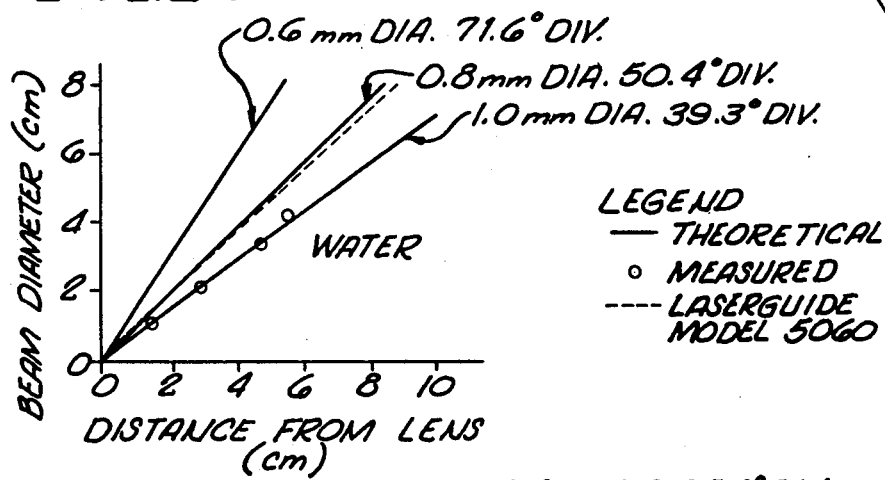
FIG. 8a shows schematically the changes of light beam diameter with respect to distance from the lens for 1 mm, 0.8 mm and 0.6 mm zirconia ball lenses in water of the present submersible ball lens fiberoptic assembly.
Figure 8B:
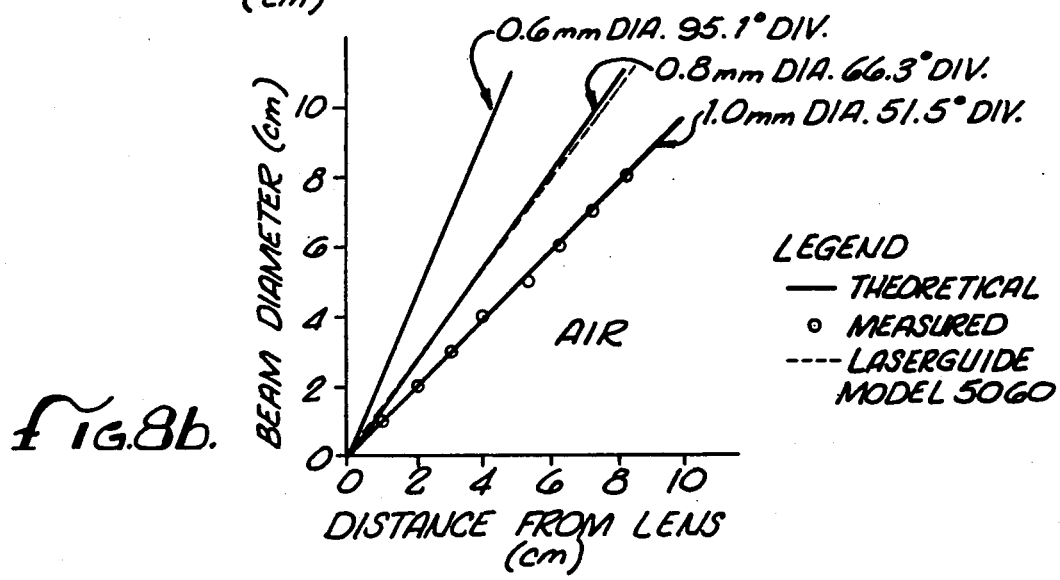
FIG. 8b shows schematically the changes of light beam diameter with respect to distance from lens for 1 mm, 0.8 mm and 0.6 mm zirconia ball lenses in air of the present submersible ball lens fiberoptic assembly.

Beam diameter plots for 1 mm, 0.8 mm and 0.6 mm ball lenses in water and in air are shown in FIGS. 8A and 8B, respectively. The full angle of the beam divergence is given next to each curve. These angles are smaller when the ball lens is submerged because water reduces the refraction of rays at the output surface. The measured values for the 1 mm ball lens are in agreement with the theoretical prediction. By way of comparison, the Laserguide Microlens Model 5060 has the same divergence as that predicted for an 800 micron diameter ball lens.

Referring now to FIGS. 9A, 9B and 9C, there is shown another preferred embodiment of the submersible lens fiberoptic system of the present invention which can be used in conjunction with side looking fiberoptic scopes for treatment of areas inaccessible to a "forwarding looking" lens. In this embodiment, the lens is a hemisphere lens made of zirconia and its spherical surface faces the optical fiber end. This type of submersible lens fiberoptic system can produce an output beam at angles up to 120° from the fiber axis. If air is maintained at the plane surface, total internal reflection (TIR) would occur for beam deflection up to 90°. At larger angles a reflective coating would be required. FIGS. 9A, 9B and 9C show the different arrangements under which the output beams of the system are at angles 60°, 90°0 and 120° from the fiber axis, respectively.

FIG. 10 shows an embodiment of the housing 30 used to fix the fiber jacket 22 and lens 20 of the side looking submersible lens fiberoptic assembly. The housing 30, besides the sleeve configuration 23 discussed in the forward looking assembly, further includes a top cover portion 25 which has a circular opening 27 on its side functioning as a light output passage, and an air cap 26 fitted on the hemisphere lens 20 to provide an air chamber 28 for the plane surface of the lens. The top cover portion is preferably made of plastic material such as epoxy. The top cover portion can be formed in the following way. The fiber system and lens with an air cap are first held by an appropriate device and correct alignment of the sphere to the fiber is made. Then, the lens is fixed to the fiber system by a waxing fixture and put into a silicon rubber mold for casting epoxy. After the lens is fixed with the fiber system by means of epoxy top cover 25, the fiber jacket 22 is unscrewed from the assembly and the wax is removed with ether or hot water to provide a air chamber 24 between the lens and fiber. Finally, the fiber is cleaned and threaded back to a proper focus for use.

Of course, some modifications as to the top cover are possible without departing from the invention concept while the present invention has been described. It is intended to cover in the appended claims all such modifications within the spirit of the invention.

What is claimed is:

1. A submersible lens fiberoptic assembly for producing a rapidly divergent light output for treating a relatively large tissue area at a short distance, comprising:

an optical fiber with an end face for emitting light energy, a fiber jacket means for protecting said optical fiber, a ball lens having a uniform index of refraction greater than 2 for light in a wavelength of 630 nm and positioned to allow said fiber end face to be substantially located at the back focal point of said ball lens, for focusing the light beam from said optical fiber inside itself and producing a rapidly divergent beam of light with substantially uniform light distribution, and a housing means fixed to said fiber jacket means surrounding said ball lens and said end face of said optical fiber, and providing an opening for exposing the output surface of said lens to the outside.

2. A submersible lens fiberoptic assembly as claimed in claim 1, wherein said housing means and said fiber jacket means are in threaded connection so that the distance between the optical fiber end and said ball lens is adjustable.

3. A submersible lens fiberoptic assembly as claimed in claim 1, wherein said ball lens is made of zirconia material.

4. A submersible lens fiberoptic assembly as claimed in claim 3, wherein said housing means and said fiber jacket means are in threaded connection.

5. A submersible lens fiberoptic assembly as claimed in claims 1 or 3, wherein said lens has a size in a range from 0.6 mm to 1 mm diameter.

* * * * *